US012698249B2

(12) United States Patent
Li et al.

(10) Patent No.: US 12,698,249 B2
(45) Date of Patent: Aug. 4, 2026

(54) SYSTEMS AND METHODS FOR A REFINEMENT PROCESSING OF XYLITOL FERMENTATION BROTH

(71) Applicant: ZHEJIANG HUAKANG PHARMACEUTICAL CO., LTD., Quzhou (CN)

(72) Inventors: Mian Li, Quzhou (CN); Ni Zhen, Quzhou (CN); Jiaxing Luo, Quzhou (CN); Changhui Hu, Quzhou (CN); Qiang Wu, Quzhou (CN); Wulong Yang, Quzhou (CN); Fangming Zeng, Quzhou (CN)

(73) Assignee: ZHEJIANG HUAKANG PHARMACEUTICAL CO., LTD., Quzhou (CN)

( * ) Notice: Subject to any disclaimer, the term of this patent is extended or adjusted under 35 U.S.C. 154(b) by 514 days.

(21) Appl. No.: 18/349,985

(22) Filed: Jul. 11, 2023

(65) Prior Publication Data

US 2023/0348349 A1      Nov. 2, 2023

Related U.S. Application Data

(63) Continuation-in-part of application No. PCT/CN2022/125221, filed on Oct. 13, 2022.

(30) Foreign Application Priority Data

Dec. 29, 2021    (CN) ......................... 202111641269.4

(51) Int. Cl.
*C07C 29/78* (2006.01)

(52) U.S. Cl.
CPC .................................. *C07C 29/78* (2013.01)

(58) Field of Classification Search
None
See application file for complete search history.

(56) References Cited

U.S. PATENT DOCUMENTS 12,006,281 B2 *  6/2024  Li ......................... C09B 67/006
2006/0110811 A1  5/2006  Kim
(Continued)

FOREIGN PATENT DOCUMENTS

CN        101538589 A      9/2009
CN        101643752 A      2/2010
(Continued)

OTHER PUBLICATIONS

Wei, Jinchao et al., Purification and Crystallization of Xylitol From Fermentation Broth of Corncob Hydrolysates, Frontiers of Chemical Engineering in China, 4(1): 57-64, 2010.
(Continued)

*Primary Examiner* — John J Figueroa
(74) *Attorney, Agent, or Firm* — METIS IP LLC

(57) ABSTRACT

The present disclosure provides a system and method for a refinement processing of xylitol fermentation broth. The system includes a fermentation component, a filtration and impurity removal component, and a refinement component. The fermentation component is configured to perform a fermentation processing on a raw material containing xylitol to obtain sediments and supernatant fermentation broth. The filtration and impurity removal component includes a ceramic membrane filter, a nanofiltration membrane filter, an activated carbon filter, and ion exchange columns. The ceramic membrane filter is configured to filter the supernatant fermentation broth to obtain ceramic membrane discharge liquid. The nanofiltration membrane filter is configured to perform a nanofiltration membrane filtration processing on the ceramic membrane discharge liquid to obtain nanofiltration liquid. The activated carbon filter is
(Continued)

configured to perform an activated carbon filtration processing on the nanofiltration liquid to obtain activated carbon discharge liquid. The ion exchange columns are configured to perform an ion exchange processing on the activated carbon discharge liquid to obtain xylitol ion exchange liquid. The refinement component is configured to perform the refinement processing on the xylitol ion exchange liquid to obtain a xylitol crystal product.

19 Claims, 3 Drawing Sheets

(56) References Cited

U.S. PATENT DOCUMENTS

| | | | | |
|---|---|---|---|---|
| 2011/0039320 A1* | 2/2011 | Li | | C12P 7/10 |
| | | | | 435/165 |
| 2015/0087038 A1* | 3/2015 | Utsunomiya | | B01D 3/002 |
| | | | | 435/158 |
| 2021/0395174 A1* | 12/2021 | Yang | | B01D 21/262 |

FOREIGN PATENT DOCUMENTS

| | | | |
|---|---|---|---|
| CN | 101863737 | A | 10/2010 |
| CN | 102241707 | A | 11/2011 |
| CN | 102249855 | A | 11/2011 |
| CN | 102268490 | A | 12/2011 |
| CN | 102676606 | A | 9/2012 |
| CN | 102839202 | A | 12/2012 |
| CN | 104086365 | A | 10/2014 |
| CN | 104357492 | A | 2/2015 |
| CN | 106748657 | A | 5/2017 |
| CN | 108949839 | A | 12/2018 |
| CN | 112707793 | A | 4/2021 |
| CN | 114478191 | A | 5/2022 |
| JP | H01215293 | A | 8/1989 |

OTHER PUBLICATIONS

Notice of Rejection in Japanese Application No. 2023-550085 mailed on Sep. 3, 2024, 37 pages.
International Search Report in PCT/CN2022/125221 mailed on Jan. 9, 2023, 7 pages.

* cited by examiner

SYSTEMS AND METHODS FOR A REFINEMENT PROCESSING OF XYLITOL FERMENTATION BROTH

CROSS-REFERENCE TO RELATED APPLICATIONS

This application is a continuation-in-part application of International Application No. PCT/CN2022/125221, filed on Oct. 13, 2022, which claims priority of Chinese Patent Application No. 202111641269.4, filed on Dec. 29, 2021, the entire contents of each of which is incorporated herein by reference.

TECHNICAL FIELD

The present disclosure relates to the technical field of xylitol preparation, in particular, to systems and methods for a refinement processing of xylitol fermentation broth.

BACKGROUND

Xylitol is a pentose (five-carbon) sugar alcohol. At present, in industrial production, xylitol is commonly produced by the chemical hydrogenation of xylose. Although reaction conditions of biological conversion are mild, there are still some technical bottlenecks. At present, xylitol is prepared by a biological method, which generally takes biomass resources such as corncobs, straws, etc., as raw materials, and obtains hemicellulose hydrolyzate after acid hydrolysis. Since xylose concentration in hydrolyzate is lower after acid hydrolysis, the hydrolyzate cannot be directly used as raw material liquid for biological fermentation. Therefore, hydrolyzate used as the raw material liquid needs to be concentrated, and a commonly used process is evaporation and concentration. During the process mentioned above, sugar, protein, and other substances in the raw material may undergo a Maillard reaction to cause the color of the raw material liquid to be deepened. Fermentation with the raw material prepared by the process also results in a dark color of final fermentation broth, which greatly hinders subsequent refinement processing of the fermentation broth.

Therefore, it is desirable to provide systems and methods for a refinement processing of xylitol fermentation broth, so as to process the fermentation broth better and obtain a xylitol crystal product satisfying a requirement through the preparation.

SUMMARY

One or more embodiments of the present disclosure provide a system for a refinement processing of xylitol fermentation broth. The system includes a fermentation component, a filtration and impurity removal component, and a refinement component. The fermentation component is configured to perform a fermentation processing on a raw material containing xylitol to obtain sediments and supernatant fermentation broth. The filtration and impurity removal component includes a ceramic membrane filter, a nanofiltration membrane filter, an activated carbon filter, and ion exchange columns. The ceramic membrane filter is configured to filter the supernatant fermentation liquid to obtain ceramic membrane discharge liquid. The nanofiltration membrane filter is configured to perform a nanofiltration membrane filtration processing on the ceramic membrane discharge liquid to obtain nanofiltration liquid. The activated carbon filter is configured to perform an activated carbon filtration processing on the nanofiltration liquid to obtain activated carbon discharge liquid. The ion exchange columns are configured to perform an ion exchange processing on the activated carbon discharge liquid effluent to obtain xylitol ion exchange liquid. The refinement component is configured to perform the refinement processing on the xylitol ion exchange liquid to obtain a xylitol crystal product.

One or more embodiments of the present disclosure provide a method for a refinement processing of xylitol fermentation broth, which is implemented on a system for the refinement processing of the xylitol fermentation broth. The method includes the following steps: step 1, performing an impurity removal, rinsing, and acidolysis processing on a raw material containing xylitol to obtain fermentation raw material liquid, obtaining xylitol fermentation broth by performing a fermentation processing using genetic engineering bacteria after performing a concentration processing on the fermentation raw material liquid until a xylose concentration is greater than a preset concentration; and performing a standing stratification processing on the xylitol fermentation broth to obtain sediments and supernatant fermentation broth respectively; step 2, performing a filtration processing on the supernatant fermentation broth through a ceramic membrane filter to obtain ceramic membrane discharge liquid excluding bacteria and large particle impurities; step 3, conveying the ceramic membrane discharge liquid to a nanofiltration membrane filter for a nanofiltration membrane filtration processing to retain impurity molecules with a molecular weight greater than a preset value to obtain nanofiltration liquid; step 4, performing an activated carbon filtration processing on the nanofiltration liquid by using activated carbons, and then passing through ion exchange columns in sequence for an ion exchange processing to obtain xylitol ion exchange liquid; step 5, performing the refinement processing on the xylitol ion exchange liquid through a refinement component to obtain a xylitol crystal product.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
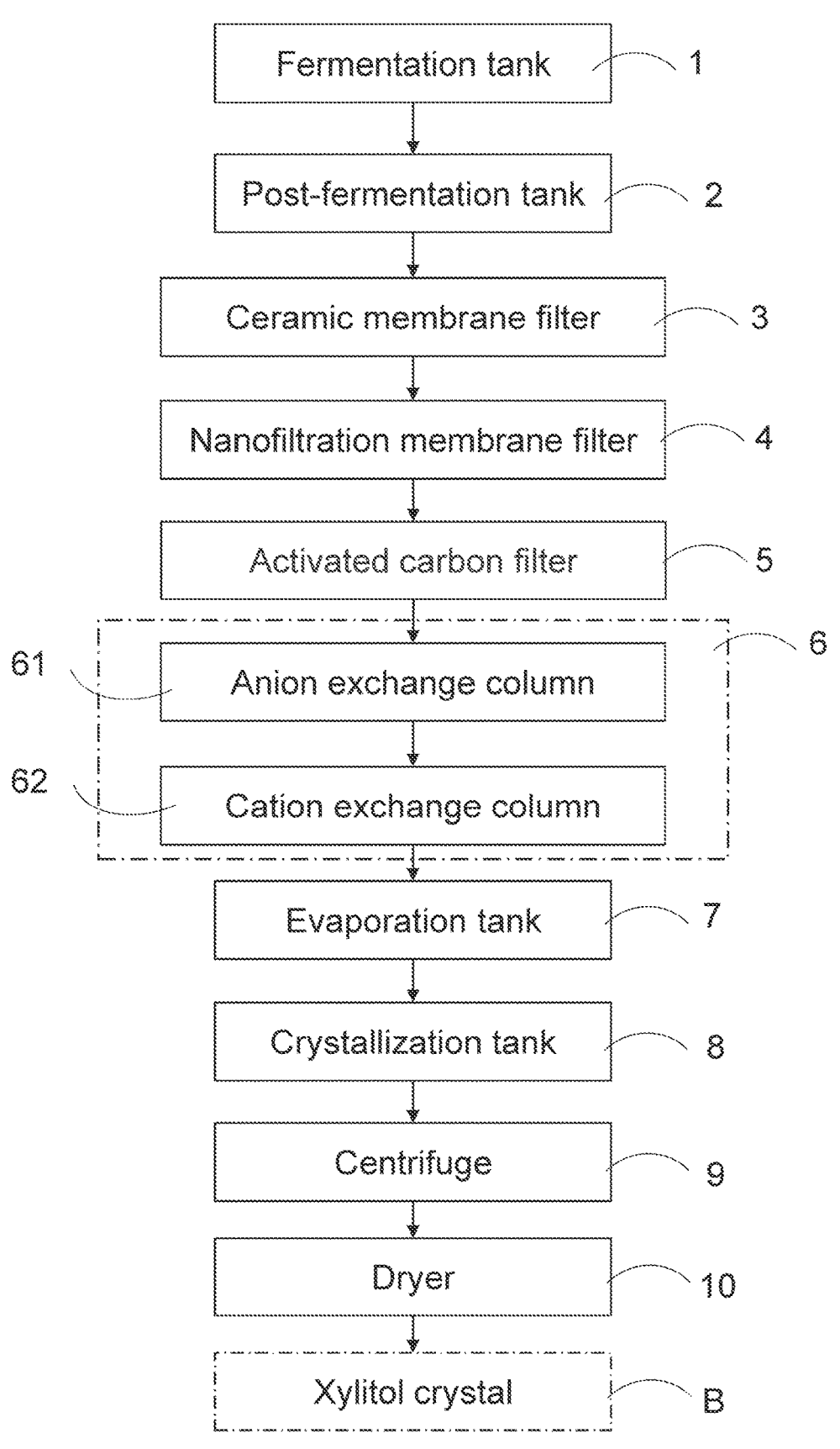
FIG. 1 is a schematic diagram illustrating an exemplary system for a refinement processing of xylitol fermentation broth according to some embodiments of the present disclosure.

In order to more clearly illustrate the technical solutions of the embodiments of the present disclosure, the following briefly introduces the drawings that need to be used in the description of the embodiments. Obviously, the accompanying drawings below are only some examples or embodiments of the present disclosure, and those skilled in the art may apply the present disclosure to other similar scenarios according to these accompanying drawings without creative effort. Unless obviously obtained from the context or the context illustrates otherwise, the same numeral in the drawings refers to the same structure or operation.

It should be understood that "system", "device", "unit" and/or "module" as used herein is a method for distinguishing different components, elements, parts, parts, or assemblies of different levels. However, the words may be replaced by other expressions if other words can achieve the same purpose.

As shown in the present disclosure and the claims, unless the context clearly suggests exceptional circumstances, the words "a", "an" and/or "the" do not specifically refer to the singular, but may also include the plural. In general, the terms "comprise," "comprises," "comprising," "include," "includes," and/or "including," merely prompt to include operations and elements that have been clearly identified, and these operations and elements do not constitute an exclusive listing. The methods or devices may also include other operations or elements.

Flowcharts are used in the present disclosure to illustrate operations performed by a system according to some embodiments of the present disclosure. It should be understood that the preceding or following operations are not necessarily performed in the exact order. Instead, various steps may be processed in reverse order or simultaneously. At the same time, other operations may be added to these procedures, or a certain step or steps may be removed from these procedures.

Xylitol is a kind of pentose (five-carbon) sugar alcohol, which is the sweetest sweetener in polyols. A flavor cooling and sweetness are equivalent to those of sucrose. A heat quantity of the Xylitol is 40% of that of the sucrose with an equal weight, which is an edible food additive as a substitute for sucrose and glucose. At present, in industrial production, xylitol is commonly produced by chemical hydrogenation of xylose, which has problems such as expensive production equipment, harsh production conditions, complicated purification, difficult catalyst recovery caused by deactivation, high energy consumption, serious environmental pollution, etc. A biological method may not only produce high-purity xylitol from xylose as a raw material but also produce xylitol from hemicellulose in crops such as straws, corncobs, bagasse, etc., as the raw material through a hydrolysis and fermentation processing. On the one hand, the high-purity xylitol is produced, on the other hand, a transformation of agricultural waste to high-value-added xylitol is achieved, and a cost of raw material purification may be reduced while saving resources. However, since xylose concentration in hydrolyzate is lower after an acid hydrolysis processing is performed, the hydrolyzate cannot be directly used as raw material liquid for biological fermentation. Therefore, the hydrolyzate used as the raw material liquid needs to be concentrated, and an evaporation and concentration technology is commonly used. In the concentration processing, sugar, protein, and other substances in the raw material may undergo a Maillard reaction to cause the color of the raw material liquid to be deepened. Performing a fermentation processing with the raw material prepared using the evaporation and concentration technology also results in a dark color of final fermentation broth, which greatly hinders subsequent refinement processing of fermentation broth.

Accordingly, some embodiments of the present disclosure provide systems and methods for a refinement processing of xylitol fermentation broth. An amount of the activated carbons may be significantly reduced while ensuring decolorization and transmittance by performing a filtration, decolorization, evaporation, crystallization, centrifugation, and drying processing on the xylitol fermentation broth in sequence. Furthermore, a pH value of material liquid may be increased, so that an electrical conductivity may be significantly reduced and a load of a subsequent ion exchange processing may also be reduced to obtain a xylitol crystal product satisfying a requirement.

FIG. 1 is a schematic diagram illustrating a system for an exemplary refinement processing of xylitol fermentation broth according to some embodiments of the present disclosure. Arrows in FIG. 1 illustrate flow directions of materials in the system.

In some embodiments, the system for the refinement processing of the xylitol fermentation broth includes a fermentation component, a filtration and impurity removal component, and a refinement component.

The fermentation component may be configured to ferment a raw material. In some embodiments, the fermentation component may be configured to ferment a raw material containing xylitol to obtain sediments and supernatant fermentation broth.

In some embodiments, as illustrated in FIG. 1, the fermentation component may include a fermentation tank 1 and a post-fermentation tank 2. The fermentation tank 1 may be configured to perform a fermentation processing on the raw material containing xylitol to obtain the xylitol fermentation broth. The post-fermentation tank 2 may be configured to store the xylitol fermentation broth and perform a standing stratification processing on the xylitol fermentation broth to obtain the sediments and the supernatant fermentation broth respectively. In some embodiments, microbes for the fermentation of the raw material may be added in the fermentation tank 1, and the raw material containing xylitol (such as a corncob, etc.) is fermented in the fermentation tank 1 to obtain the xylitol fermentation broth. The xylitol fermentation broth is transported to the post-fermentation tank 2, and the xylitol fermentation broth is processed through standing and stratification processing to obtain the sediments and the supernatant fermentation broth.

In some embodiments, as illustrated in FIG. 1, the filtration and impurity removal component may include a ceramic membrane filter 3, a nanofiltration membrane filter 4, an activated carbon filter 5, and ion exchange columns 6. The ceramic membrane filter 3 may be configured to filter the supernatant fermentation broth to obtain ceramic membrane discharge liquid and large particle impurities, bacteria with a large size, etc. The nanofiltration membrane filter 4 may be configured to perform a nanofiltration membrane filtration processing on the ceramic membrane discharge liquid to obtain nanofiltration liquid. The nanofiltration membrane filter 4 may retain impurity molecules with a molecular weight greater than a preset value. The preset value may be set according to requirements, and different settings may be made for the nanofiltration membrane filter 4 based on different preset values. For example, a nanofiltration membrane with a different parameter may be replaced or the like. The activated carbon filter 5 may be configured to perform an activated carbon filtration processing on the nanofiltration liquid to obtain ceramic membrane discharge liquid. The ion exchange columns 6 are configured to perform an ion exchange processing on the ceramic membrane discharge liquid to obtain xylitol ion exchange liquid.

In some embodiments, the refinement component may be configured to perform a refinement processing on the xylitol ion liquid to obtain a xylitol crystal product.

In some embodiments, as illustrated in FIG. 1, the refinement component may include an evaporation tank 7, a crystallization tank 8, a centrifuge 9, and a dryer 10. The evaporation tank 7 may be configured to perform an evaporation and concentration processing on the xylitol ion exchange liquid. The crystallization tank 8 may be configured to perform a crystallization processing on the xylitol ion exchange liquid after the evaporation and concentration processing is performed to obtain xylitol massecuite. The centrifuge 9 may be configured to perform a separation processing on the xylitol massecuite to obtain a crystal xylitol and mother liquor respectively. The dryer 10 may be configured to obtain a refined xylitol crystal B product through drying of the crystal xylitol.

In some embodiments, as illustrated in FIG. 1, the ion exchange columns 6 may include an anion exchange column 61 and a cation exchange column 62. The ion exchange columns 6 may be configured for an ion exchange reaction. The xylitol ion exchange liquid may be obtained by performing the ion exchange processing on the nanofiltration liquid filtered in the activated carbon filtration processing through the anion exchange column 61 and the cation exchange column 62.

In some embodiments, the raw material of xylitol is reacted in the fermentation component, the filtration and impurity removal component, and the refinement component in sequence to obtain the xylitol crystal product. A transmittance of the material liquid may be greatly improved by using the filtration and impurity removal component. The xylitol crystal product obtained by the refinement component satisfies the requirement, and the crystal is of high purity and has a regular and smooth surface.

In some embodiments, the system for the refinement processing of the xylitol fermentation broth may further include a detection device (not shown in the figure). The detection device, such as a transmittance meter, a pH tester, a conductivity meter, etc., may be configured to detect a physico-chemical parameter of the nanofiltration liquid. The physico-chemical parameter of the nanofiltration liquid may include a transmittance, a pH value, a conductivity value, etc. In some embodiments, the detection device may be arranged between the nanofiltration membrane filter 4 and the activated carbon filter 5.

In some embodiments, the detection device may also include a high chroma resolution camera. The high chroma resolution camera may be configured to capture a chroma image. The chroma image refers to an image of the nanofiltration liquid passing through the activated carbon filter, which is used to reflect a color of the nanofiltration liquid and to evaluate a decolorization effect. The decolorization effect refers to a decolorization degree of liquid. More details about the evaluation of the decolorization effect may be found elsewhere in the present disclosure.

Figure 2:
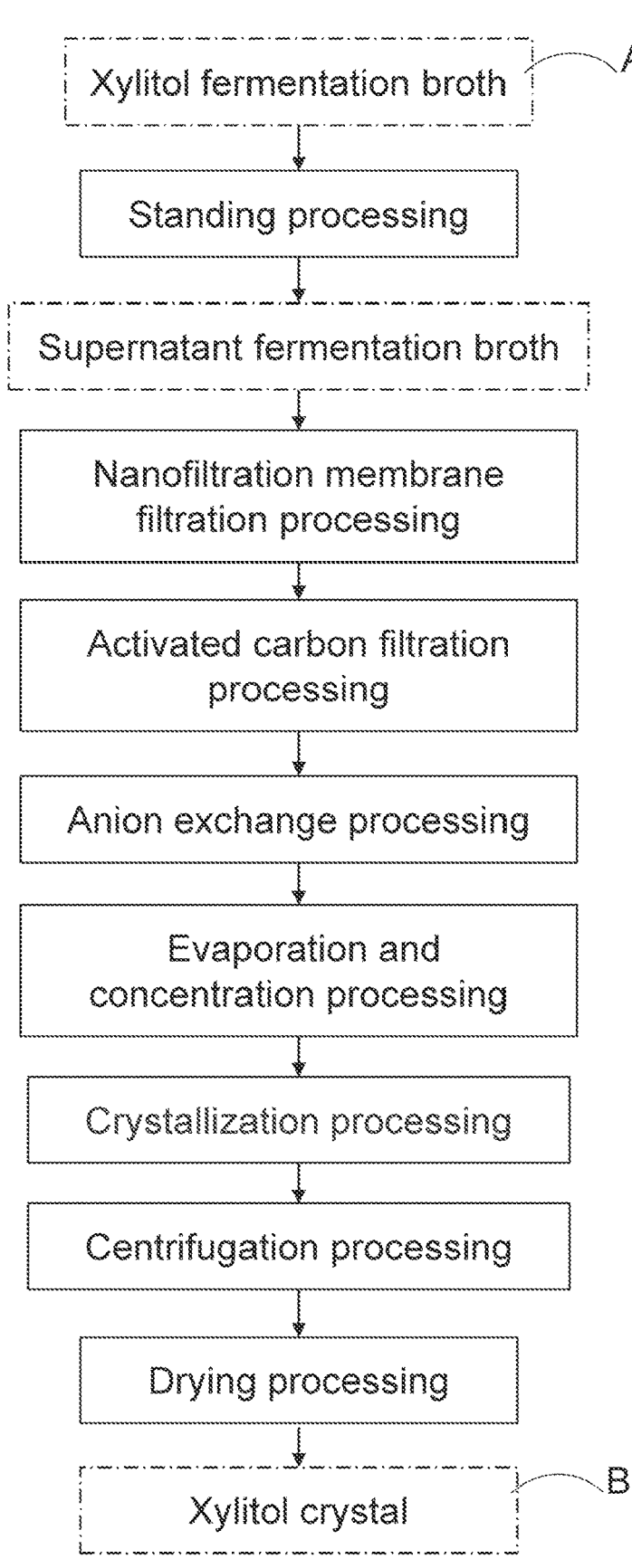
FIG. 2 is a flowchart illustrating an exemplary method for a refinement processing of xylitol fermentation broth according to some embodiments of the present disclosure.

FIG. 2 is a flowchart illustrating an exemplary method for a refinement processing of xylitol fermentation broth according to some embodiments of the present disclosure.

Some embodiments of the present disclosure also provide a method for a refinement processing of xylitol fermentation broth. The method may be implemented on a system for a refinement processing of xylitol fermentation broth mentioned above, and the method includes the following steps:

Step 1, an impurity removal, rinsing, and acidolysis processing are performed on a raw material containing xylitol to obtain fermentation raw material liquid, xylitol fermentation broth A is obtained by performing a fermentation processing using genetic engineering bacteria after performing a concentration processing on the fermentation raw material liquid until a xylose concentration is greater than a preset concentration, and a standing stratification processing is performed on the xylitol fermentation broth to obtain sediments and supernatant fermentation broth respectively.

Step 2, a filtration processing is performed on the supernatant fermentation broth through a ceramic membrane filter 3 to obtain a ceramic membrane discharge liquid excluding bacteria and large particle impurities.

Step 3, the ceramic membrane discharge liquid is conveyed to a nanofiltration membrane filter 3 for a nanofiltration membrane filtration processing to retain impurity molecules with a molecular weight greater than a preset value to obtain nanofiltration liquid.

Step 4, an activated carbon filtration processing is performed on the nanofiltration liquid by using activated carbons, and ion exchange columns 6 are passed through in sequence for an ion exchange processing to obtain xylitol ion exchange liquid.

Step 5, the refinement processing is performed on the xylitol ion exchange liquid through a refinement component to obtain a xylitol crystal B product.

In some embodiments, in step 5, the refinement processing includes performing an evaporation and concentration processing, and then performing a cooling and crystallization processing to obtain xylitol massecuite, performing a centrifugation processing on the xylitol massecuite to obtain a crystal xylitol and mother liquor, and performing a drying processing on the crystal xylitol to obtain a refined xylitol crystal B product.

In some embodiments, the method for the refinement processing of the xylitol fermentation broth further includes step 6. In step 6, the mother liquor obtained during the refinement processing is mixed with the xylitol ion exchange liquid and an evaporation and concentration processing is performed on the mixed mother liquor and the xylitol ion exchange liquid to recycle the mother liquor.

In some embodiments, in step 1, a solid content of the fermentation raw material liquid is within a range of 10%~13%, an electrical conductivity of the fermentation raw material liquid is within a range of 14,000 μs/cm~16,000 μs/cm, and a pH value of the fermentation raw material liquid is within a range of 6.0~6.8. In some embodiments, in step 1, the solid content of the fermentation raw material liquid is 12%, the electrical conductivity of the fermentation raw material liquid is 15000 μs/cm, and the pH value of the fermentation raw material liquid is 6.5. In some embodiments, in step 1, the solid content of the fermentation raw material liquid is 11%, the electrical conductivity of the fermentation raw material liquid is 15500 μs/cm, and the pH value of the fermentation raw material liquid is 6.3.

In some embodiments, in step 1, the raw material containing xylitol includes a corncob. A xylose content of the corncob may account for more than 25% of a dry weight of a plant, thus, the corncob is a good raw material containing xylitol. The raw material containing xylitol may also include a crop straw, bagasse, etc.

In some embodiments, in step 1, the preset concentration may be 500 g/L. After the fermentation raw material liquid is concentrated until the xylose concentration is greater than the preset concentration of 500 g/L, the xylitol fermentation broth is obtained through the fermentation processing with genetic engineering bacteria. In some embodiments, in step 1, the fermentation raw material liquid may be concentrated until the xylose concentration is 550 g/L. In some embodiments, in step 1, the fermentation raw material liquid may be concentrated until the xylose concentration is 600 g/L.

In some embodiments, in step 2, a feed temperature is within a range of 36° C.-48° C., and a filtration pressure is within a range of 0.2 MPa-0.4 Mpa. In some embodiments, in step 2, the feed temperature may be 40° C., and the filtration pressure may be 0.3 Mpa. In some embodiments, in step 2, the feed temperature may be 42° C., and the filtration pressure may be 0.33 Mpa. The supernatant fermentation broth is processed through the filtration processing by the ceramic membrane filter 3 to obtain ceramic membrane discharge liquid excluding bacteria and large particle impurities. By controlling the feed temperature and the filtration pressure, the ceramic membrane discharge liquid meeting a standard may be obtained.

In some embodiments, in step 3, the preset value is 400 Da. The ceramic membrane discharge liquid is conveyed to a nanofiltration membrane filter for a nanofiltration membrane filtration processing, so as to retain the impurity molecules with the molecular weight greater than the preset value of 400 Da to obtain the nanofiltration liquid.

In some embodiments, in step 3, a transmittance of the nanofiltration liquid is within a range of 20%~40%.

In some embodiments, in step 3, a feed temperature of the nanofiltration membrane filtration processing is within a range of 36° C.~48° C., and a filtration pressure is within a range of 2.5 MPa~3.3 MPa. In some embodiments, in step 3, the feed temperature of the nanofiltration membrane filtration processing may be 40° C., and the filtration pressure may be 3.0 MPa. In some embodiments, in step 3, the feed temperature of the nanofiltration membrane filtration processing may be 42° C., and the filtration pressure may be 2.8 MPa.

In some embodiments, in step 4, activated carbons are used to filter the nanofiltration liquid through an activated carbon filtration processing, and an amount of the activated carbons is within a range of 0.5%~1.0%. In some embodiments, in step 4, the activated carbons are used to filter the nanofiltration liquid through the activated carbon filtration processing, and the amount of the activated carbons may be 0.8%. In some embodiments, in step 4, the activated carbons are used to filter the nanofiltration liquid through the activated carbon filtration processing, and the amount of the activated carbons may be 0.7%.

In some embodiments, in step 4, after the nanofiltration liquid is filtered, the xylitol ion exchange liquid is obtained by performing the ion exchange processing on the filtered nanofiltration liquid through ion exchange columns, and the electrical conductivity of the xylitol ion exchange liquid is less than 20 µs/cm.

In some embodiments, a refraction of the xylitol ion exchange liquid is within a range of 78%~82% through the evaporation and concentration processing.

In some embodiments, a xylitol crystal product satisfying the requirement may be obtained by processing the xylitol fermentation broth through an accurate controlling of an implementation condition of the method for the refinement processing. The crystal is of high purity and has a regular and smooth surface. The transmittance of the xylitol fermentation broth may be more than 90% by processing the xylitol fermentation broth through the ceramic membrane filter, the nanofiltration membrane filter, and the activated carbon filter. At the same time, the pH value of the material liquid may be increased, the electrical conductivity is significantly reduced by absorbing some ions, and the load of a subsequent ion exchange process is reduced.

In some embodiments, the method for the refinement processing of the xylitol fermentation broth also includes determining a product quality of the nanofiltration liquid based on a physico-chemical parameter of the nanofiltration liquid and a nanofiltration membrane parameter, and determining a filtration parameter of the activated carbon filter based on the product quality of the nanofiltration liquid. More details about the physico-chemical parameter of the nanofiltration liquid and the nanofiltration membrane parameter may be found in related descriptions hereinabove. The product quality of the nanofiltration liquid refers to the physico-chemical parameter of the nanofiltration liquid including the transmittance, the pH value, the electrical conductivity value, etc. The filtration parameter of the activated carbon filter may include the amount of the activated carbons and a processing condition (e.g., a temperature during filtration, etc.).

In some embodiments, the determining a product quality of the nanofiltration liquid based on the physico-chemical parameter of the nanofiltration liquid and the nanofiltration membrane parameter includes determining the product quality based on the transmittance, the pH value, the electrical conductivity value, etc., through a preset table.

An exemplary preset table is as follows:

| Transmittance | PH value | Electrical conductivity value | Quality |
| --- | --- | --- | --- |
| a1 | b1 | c1 | d1 |
| . . . | . . . | . . . | . . . |

In some embodiments, the determining a filtration parameter of the activated carbon filter based on the product quality of the nanofiltration liquid includes determining an adjustment amount based on the preset table. For example, the preset table may specify a quantity range and a temperature range of the activated carbons when the quality is X, and the adjustment amount is determined according to the range specified in the preset table and a current parameter.

In some embodiments, the preset table is built based on historical data. For example, based on the historical data, it is possible to know how to adjust the filtration parameter of the activated carbon filter when the nanofiltration liquid is of a certain quality, so as to obtain a better filtration effect to build the preset table.

In some embodiments, the method for the refinement processing of xylitol fermentation broth further includes during the filtration processing of the nanofiltration liquid through the activated carbon filter, evaluating a decolorization effect based on a chroma image sequence including chroma images captured at a plurality of time points in the filtration process, and adjusting the filtration parameter of the activated carbon filter in response to a determining that the decolorization effect does not satisfy a preset requirement of the decolorization effect. In some embodiments, the adjusting the filtration parameter of the activated carbon filter may include increasing the amount of the activated carbons, increasing or decreasing the temperature, etc.

The chroma image sequence may be an image sequence including chroma images captured at the plurality of time points in the filtration process. More details about the chroma image may be found in related descriptions hereinabove.

In some embodiments, the plurality of time points may be preset. For example, the chroma images may be captured every few minutes. In some embodiments, intervals between the time points may be adjusted according to different filtration stages. For example, intervals between the time points in an early filtration stage may be shorter (also referred to that the filtration effect is more obvious at this time, and the chroma changes significantly), and intervals between the time points in a post-filtration stage may be longer (also referred to that the filtration processing is almost completed, and the chroma almost does not change).

In some embodiments, the decolorization effect may be evaluated based on the chroma image sequence including chroma images captured at the plurality of time points in the filtration process. In some embodiments, the evaluating the decolorization effect may further include calculating a decolorization rate in a completed time period and predicting a decolorization rate in a future time period according to the chroma image sequence, and evaluating the decolorization effect based on the decolorization rate in the completed time period and the predicted decolorization rate in the future time period.

In some embodiments, the decolorization rate in a future time period may be predicted based on a decolorization rate prediction model.

In some embodiments, the decolorization rate prediction model is a model predicting the decolorization rate in the future time period. In some embodiments, the decolorization rate prediction model may be a machine learning model. In some embodiments, the decolorization rate prediction model may be a neural network model (NN), etc.

In some embodiments, an input of the decolorization rate prediction model includes a decolorization rate, an environmental temperature, and an amount of the activated carbons in the completed time period, and an output of the decolorization model includes the decolorization rate in the future time point. In some embodiments, the decolorization rate in the completed time period is not an overall average rate, but a decolorization rate calculated in each time interval (e.g., calculating the decolorization rate according to a chroma corresponding to an endpoint of a time interval) that is obtained by dividing the completed time period into a plurality of time intervals.

In some embodiments, the decolorization rate prediction model may be obtained by training a plurality of training samples with labels. For example, the plurality of training samples with labels may be input into a preliminary decolorization rate prediction model, a loss function may be constructed based on the labels and a result of the preliminary decolorization rate prediction model, and a parameter of the preliminary decolorization rate prediction model may be iteratively updated based on the loss function by using an algorithm such as a gradient descent algorithm, etc. The model training is completed when satisfying a preset condition, and a trained decolorization rate prediction model is obtained. The preset condition may be that the loss function converges, a count of iterations reaches a threshold, etc. In some embodiments, a historical decolorization process is divided into two stages. In the first stage, the decolorization rate in the completed time period is calculated. The decolorization rate is used as training data combined with the environmental temperature and the amount of the activated carbons. In the second stage, a calculated decolorization rate is designated as the label.

In some embodiments, the decolorization effect may be quickly and accurately evaluated through the decolorization rate prediction model, so that when the decolorization effect does not satisfy the preset requirement of the decolorization effect, the filtration parameter of the activated carbon filter may be precisely controlled and adjusted to make the final decolorization effect satisfy the preset requirement.

Exemplary tests of nanofiltration membranes with different interception volumes in the present disclosure are as follows:

A test manner for selecting a nanofiltration membrane in the decolorization process of the xylitol fermentation broth includes selecting nanofiltration membranes with an interception aperture of 200 Da, 400 Da, and 600 Da to perform a decolorization effect test, and selecting a nanofiltration membrane with a suitable interception aperture by performing a comprehensive evaluation on two aspects of the decolorization effect of the material liquid and an amount of the activated carbons in a subsequent secondary decolorization processing.

(1) The ceramic membrane discharge liquid in a volume of 30 L is divided into three equal parts, and each part is in a volume of 10 L. A transmittance of the ceramic membrane discharge liquid is 0%, and a pH value of the ceramic membrane discharge liquid is about 6.47.

(2) In a decolorization test for a nanofiltration membrane with an interception aperture of 200 Da, the material liquid in a volume of 10 L is added to a nanofiltration device, a processing pressure is 3.3 MPa, a flux is about 4 L/h, and a material liquid temperature is 45° C. The transmittance of the material liquid is about 48% after processed through the nanofiltration membrane. A yield of the process mentioned above is less than 50%. The transmittance of the material liquid may be increased to 96% after processed through the nanofiltration membrane with the interception aperture of 200 Da and 0.5% activated carbons are added for the processing.

(3) In a decolorization test for a nanofiltration membrane with an interception aperture of 400 Da, the material liquid in a volume of 10 L is added to the nanofiltration device, the processing pressure is 3.3 MPa, the flux is about 6 L/h, and the material liquid temperature is 45° C. The transmittance of the material liquid is about 35% after processed through the nanofiltration membrane. The yield of the process mentioned above is more than 90%. The transmittance of the material liquid may be increased to 92% after processed through the nanofiltration membrane with the interception aperture of 400 Da and 0.5% activated carbons are added for the processing.

(4) In a decolorization test for a nanofiltration membrane with an interception aperture of 600 Da, the material liquid in a volume of 10 L is added to the nanofiltration device, the processing pressure is 3.3 MPa, the flux is about 6 L/h, and the material liquid temperature is 45° C. The transmittance of the material liquid is about 17.06% after processed through the nanofiltration membrane. The yield of the process mentioned above is more than 90%. The transmittance of the material liquid may be increased to 92% after processed through the nanofiltration membrane with the interception aperture of 600 Da and about 2% activated carbons are added for the processing.

Based on a comparison result of decolorization effects of nanofiltration membranes with different interception volumes of 200 Da, 400 Da, and 600 Da, the nanofiltration membrane with an interception aperture of 400 Da is selected as the nanofiltration membrane having the best decolorization effect based on an evaluation of the decolorization effect and the amount of the activated carbons in the subsequent secondary decolorization processing comprehensively, which has a high yield and a less amount of the activated carbons in the subsequent secondary decolorization processing.

In some embodiments, a preferred nanofiltration membrane parameter may be further determined based on experimental results of the decolorization effect of the nanofiltration membranes combined with prediction results of a decolorization effect of untested nanofiltration membranes. A preset count of nanofiltration membranes with different nanofiltration membrane parameters are selected for the decolorization effect tests to obtain the decolorization effects of the selected nanofiltration membranes respectively. Decolorization effects of different untested nanofiltration membranes are predicted based on the decolorization effects of the preset count of nanofiltration membranes. The preferred nanofiltration membrane parameter is determined based on the decolorization effects of the tested nanofiltration membranes and the predicted decolorization effects of the untested nanofiltration membranes.

In some embodiments, the decolorization effect may be determined based on the decolorization effect of the material liquid and the amount of the activated carbons in subsequent secondary decolorization processing. Merely by way of example, the decolorization effect may be determined based on a preset table.

An exemplary preset table is as follows:

| Decolorization effect of material liquid | An amount of activated carbons | Decolorization effect |
|---|---|---|
| a1 | b1 | c1 |
| . . . | . . . | . . . |

The preset table may specify a decolorization effect of the material liquid and an amount of the activated carbons in subsequent secondary decolorization processing when the decolorization effect is Y, and an adjustment amount is determined according to a range of the table and a current parameter.

In some embodiments, the preset table is constructed based on historical data. For example, based on the historical data, it is possible to know how to adjust the filtration parameter when the nanofiltration liquid is of a certain decolorization effect, thereby obtaining a better decolorization effect and constructing the preset table.

In some embodiments, the nanofiltration membrane parameter corresponding to the best decolorization effect may be selected as the preferred nanofiltration membrane parameter.

In some embodiments, the decolorization effect of the nanofiltration membrane may be predicted based on a decolorization effect prediction model. For example, decolorization effect tests may be performed on nanofiltration membranes with three nanofiltration membrane parameters of 600 Da, 400 Da, and 200 Da respectively. Three experimental data may be input into the decolorization effect prediction model, and then a nanofiltration membrane parameter 150 Da to be predicted, a material liquid feature, and a nanofiltration parameter may be input into the decolorization effect prediction model to predict a predicted decolorization effect when the nanofiltration membrane parameter is 150 Da, so as to determine the preferred nanofiltration membrane parameter.

In some embodiments, the decolorization effect prediction model is a model used to predict the decolorization effect of the nanofiltration membrane. In some embodiments, the decolorization effect prediction model may be a machine learning model. In some embodiments, the decolorization effect prediction model may be a neural network model (NN), etc.

In some embodiments, an input of the decolorization effect prediction model is the material liquid feature of the ceramic membrane discharge liquid, the nanofiltration parameter, the nanofiltration membrane parameter to be predicted, a plurality sets of nanofiltration membrane parameters for which the decolorization effect tests have been completed, and decolorization effects corresponding to the nanofiltration membrane parameters. An output of the decolorization effect model is a decolorization effect of the nanofiltration membrane parameters to be predicted. The nanofiltration parameter may include a parameter in the nanofiltration membrane processing, such as a pressure, a throughput, a temperature, etc. The plurality sets of nanofiltration membrane parameters for which the decolorization effect tests have been completed may include an interception aperture of the nanofiltration membrane, etc.

More details about training of the decolorization effect prediction model may be found in descriptions of training of the decolorization rate prediction model hereinabove. A training sample of the decolorization effect prediction model is a tested nanofiltration membrane parameter, and a label is a corresponding experimental result (i.e., a corresponding decolorization effect).

In some embodiments, an optimal nanofiltration membrane parameter corresponding to the best decolorization effect is determined accurately and quickly by combining the decolorization effects of tested nanofiltration membranes with predicted decolorization effects of nanofiltration membranes with different nanofiltration membrane parameters.

The system and method for the refinement processing of xylitol fermentation broth are further illustrated through specific examples hereinafter in the present disclosure.

In some embodiments, the method for the refinement processing of xylitol fermentation broth includes the following steps:

Step 11, a preparation of xylitol fermentation broth includes taking biomass resources such as a corncob as a raw material, and performing an impurity removal, rinsing, and acidolysis processing on the raw material to obtain fermentation raw material liquid. The fermentation raw material liquid is concentrated until a xylose concentration is more than 500 g/L after the impurity removal, decolorization, etc., are performed. The xylitol fermentation broth is obtained through a fermentation processing using genetic engineering bacteria, and a solid content of the xylitol fermentation broth is 11%, an electrical conductivity is 16000 μs/cm, and a pH value is 6.2. In addition to fermentation microorganisms, the xylitol fermentation broth also includes impurities such as large particles of corn steep liquor. A color of the xylitol fermentation broth is dark, and a transmittance is 0%.

Step 12, the xylitol fermentation broth in a volume of 6 L is taken and a ceramic membrane filtration processing is performed. A membrane module retains large particle impurities and bacteria with a diameter greater than 50 nm. An average flux is 2 L/h, a filtration pressure is 0.2 MPa, and a material liquid temperature is 45° C. during the processing. The electrical conductivity of the ceramic membrane discharge liquid drops to 13460 μs/cm and a pH value of the ceramic membrane discharge liquid is 6.4 after the processing.

Step 13, a decolorization processing is performed on the ceramic membrane exchange liquid through the nanofiltration membrane filtration processing. In the processing, a nanofiltration membrane with an interception volume larger than 400 Da is selected. A processing temperature is 45° C., the filtration pressure is 3.3 MPa, and the flux is about 6 L/h. After the decolorization processing is performed through the nanofiltration membrane filtration processing, the transmittance of the nanofiltration liquid is increased from 0% to 33%, the pH value of the nanofiltration liquid is increased to 6.8, and the electrical conductivity of the nanofiltration liquid is decreased to 7588 μs/cm.

Step 14, after the processing of step 13, 0.5% activated carbon powder is added to the system for a secondary decolorization processing through the activated carbon filtration processing. Conditions include performing the decolorization processing at 60° C. for 2 hours. Secondary decolorization liquid is activated carbon discharge liquid. The pH value of the activated carbon discharge liquid is 6.9, the electrical conductivity of the activated carbon discharge liquid is dropped to 6865 μs/cm, and the transmittance of the activated carbon discharge liquid is 92.4%.

Step 15, after the secondary decolorization liquid is obtained through step 14, an ion exchange processing is performed on the secondary decolorization liquid. A discharge electrical conductivity is controlled to be less than 50 μs/cm during the ion exchange processing, and a manner of water top pressure is adopted to improve the yield of a stage process.

Step 16, an evaporation and concentration processing is performed on the ion exchange liquid until a refraction is 82%, and then a subsequent cooling crystallization processing is performed to obtain a xylitol crystal through a centrifugation and drying processing.

Figure 3:
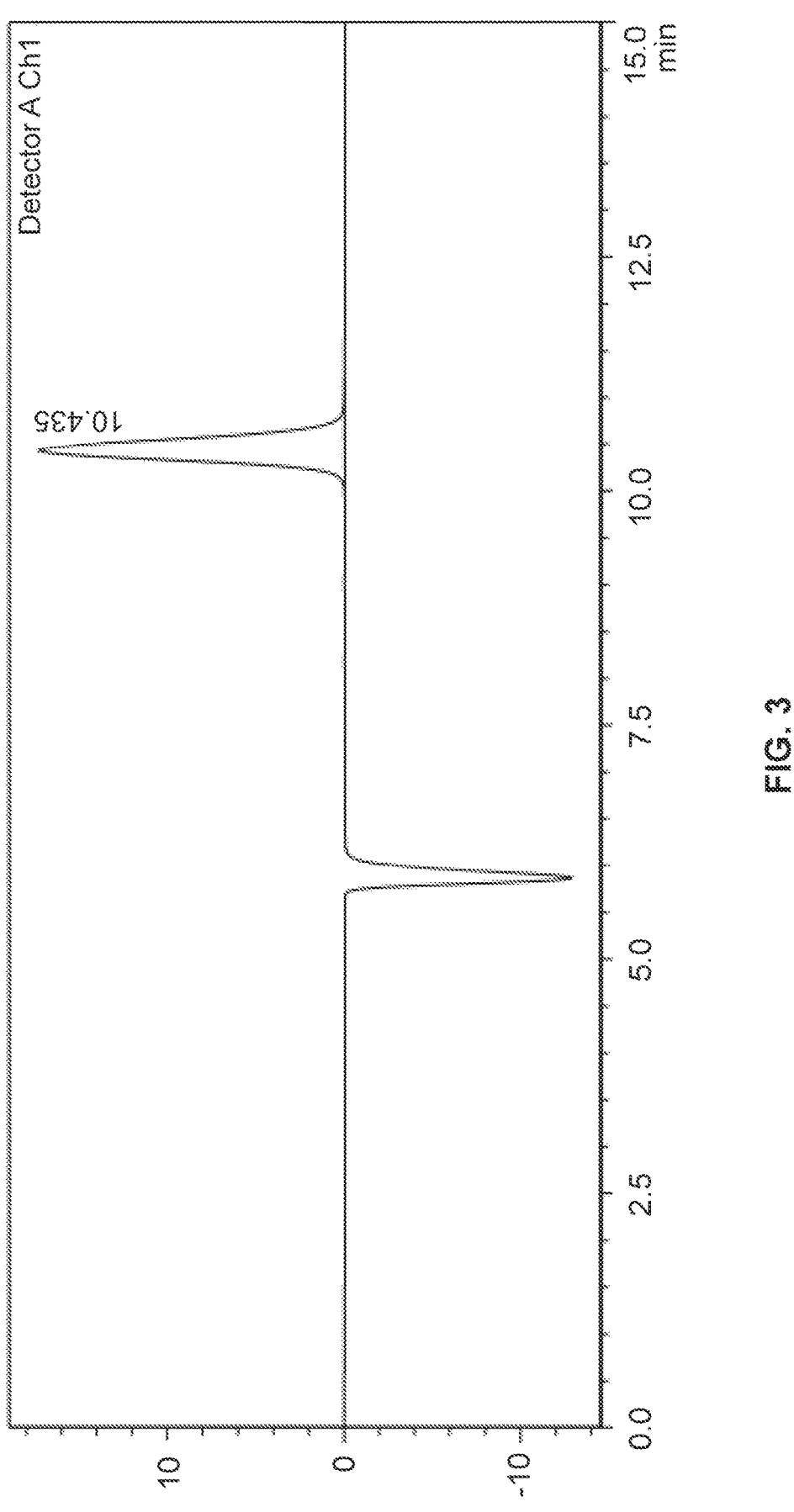
FIG. 3 is an analysis spectrum illustrating an HPLC purity of a xylitol crystal product according to some embodiments of the present disclosure.

FIG. 3 is an analysis spectrum illustrating an HPLC purity of a xylitol crystal product according to some embodiments of the present disclosure. As illustrated in FIG. 3, a xylitol crystal obtained through preparation has a white appearance, and a product purity is 99.71% based on a measurement of HPLC. Under an observation through a microscope, a crystal morphology of the xylitol crystal represents as a prismatic shape, a crystal surface is relatively regular and smooth, fine crystals adsorbed on a surface of large particles are less, and other indicators all satisfy requirements.

Having described the basic concepts above, it is clear that the above detailed disclosures are intended only as examples for technicians skilled in the art and do not constitute the qualification of this description. Although it is not explicitly stated herein, this description may be subject to various modifications, improvements and corrections by technicians skilled in the art. Such modifications, improvements and corrections are suggested in this description and therefore remain within the spirit and scope of the demonstration embodiments of the present disclosure.

Meanwhile, the present disclosure uses specific words to describe the embodiments of the present disclosure. For example, "one embodiment", "an embodiment", and/or "some embodiments" refer to a certain feature, structure, or characteristic related to at least one embodiment of the present disclosure. Therefore, it should be emphasized and noted that two or more references to "an embodiment" "an embodiment" or "an alternative embodiment" in different places in the present disclosure do not necessarily refer to the same embodiment. In addition, certain features, structures, or characteristics in one or more embodiments of the present disclosure may be properly combined.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure method does not mean that the characteristics required by the object of the present disclosure are more than the characteristics mentioned in the claims. Rather, claimed subject matter may lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." Unless otherwise stated, "about", "approximately" or "substantially" indicates that the stated figure allows for a variation of ±20%. Accordingly, in some embodiments, the numerical parameters used in the present disclosure and claims are approximations that can vary depending upon the desired characteristics of individual embodiments. In some embodiments, numerical parameters should take into account the specified significant digits and adopt the general digit reservation method. Notwithstanding that the numerical ranges and parameters setting forth the broad scope of some embodiments of the present disclosure are approximations, the numerical values set forth in the specific examples are reported as precisely as practicable.

Finally, it should be understood that the embodiments described in the present disclosure are only used to illustrate the principles of the embodiments of the present disclosure. Other modifications are also possible within the scope of the present disclosure. Therefore, by way of example and not limitation, alternative configurations of the embodiments of the present disclosure may be considered consistent with the teachings of the present disclosure. Accordingly, the embodiments of the present disclosure are not limited to the embodiments explicitly introduced and described in the present disclosure.

What is claimed is:

1. A method for a refinement processing of xylitol fermentation broth, wherein the method is implemented on a system, and the method comprises:

step 1, performing an impurity removal, rinsing, and acidolysis processing on a raw material containing xylitol to obtain fermentation raw material liquid, obtaining the xylitol fermentation broth by performing a fermentation processing using genetic engineering bacteria after performing a concentration processing on the fermentation raw material liquid until a xylose concentration is greater than a preset concentration, and performing a standing stratification processing on the xylitol fermentation broth to obtain sediments and supernatant fermentation broth respectively;

step 2, performing a filtration processing on the supernatant fermentation broth through a ceramic membrane filter to obtain ceramic membrane discharge liquid excluding bacteria and large particle impurities;

step 3, conveying the ceramic membrane discharge liquid to a nanofiltration membrane filter for a nanofiltration membrane filtration processing to retain impurity molecules with a molecular weight greater than a preset value to obtain nanofiltration liquid;

step 4, performing an activated carbon filtration processing on the nanofiltration liquid by using activated carbons, and passing through ion exchange columns in sequence for an ion exchange processing to obtain xylitol ion exchange liquid; and step 5, performing the refinement processing on the xylitol ion exchange liquid through a refinement component to obtain a xylitol crystal product.

2. The method of claim 1, further comprising:

step 6, mixing mother liquor obtained during the refinement processing with the xylitol ion exchange liquid and performing an evaporation and concentration processing on the mixed mother liquor and the xylitol ion exchange liquid to recycle the mother liquor.

3. The method of claim 1, wherein a solid content of the fermentation raw material liquid is within a range of 10%~13%, an electrical conductivity of the fermentation raw material liquid is within a range of 14,000 μs/cm~16,000 μs/cm, and a pH value of the fermentation raw material liquid is within a range of 6.0~6.8.

4. The method of claim 1, wherein the raw material containing xylitol includes a corncob.

5. The method of claim 1, wherein the preset concentration is 500 g/L.

6. The method of claim 1, wherein a feed temperature is within a range of 36° C.~48° C. and a filtration pressure is within a range of 0.2 MPa~0.4 Mpa.

7. The method of claim 1, wherein the preset value is 400 Da.

8. The method of claim 1, wherein a transmittance of the nanofiltration liquid is within a range of 20%~40%.

9. The method of claim 1, wherein a feed temperature of the nanofiltration membrane filtration processing is within a range of 36° C.~48° C. and a filtration pressure of the nanofiltration membrane filtration processing is within a range of 2.5 Mpa~3.3 MPa.

10. The method of claim 1, wherein an amount of the activated carbons is within a range of 0.5%~1.0%.

11. The method of claim 1, wherein an electrical conductivity of the xylitol ion exchange liquid is less than 20 μs/cm.

12. The method of claim 1, wherein the refinement processing in the step 5 comprises:

performing an evaporation and concentration processing and then performing a cooling and crystallization processing to obtain xylitol massecuite;

performing a centrifugation processing on the xylitol massecuite to obtain a crystal xylitol and mother liquor; and performing a drying processing on the crystal xylitol to obtain a refined xylitol crystal product.

13. The method of claim 12, wherein a refraction of the xylitol ion exchange liquid is within a range of 78%~82% through the evaporation and concentration processing.

14. The method of claim 1, wherein the method further includes:

determining a product quality of the nanofiltration liquid based on a physico-chemical parameter of the nanofiltration liquid and a nanofiltration membrane parameter; and determining a filtration parameter of an activated carbon filter based on the product quality of the nanofiltration liquid.

15. The method of claim 14, wherein the method further includes:

during the filtration processing of the nanofiltration liquid through the activated carbon filter, evaluating a decolorization effect based on a chroma image sequence including chroma images captured at a plurality of time points in the filtration process; and adjusting the filtration parameter of the activated carbon filter in response to a determining that the decolorization effect does not satisfy a preset requirement of the decolorization effect.

16. The method of claim 15, wherein the adjusting the filtration parameter of the activated carbon filter includes increasing the amount of the activated carbons, increasing or decreasing a temperature.

17. The method of claim 15, wherein the decolorization effect is evaluated based on the chroma image sequence including chroma images captured at the plurality of time points in the filtration process.

18. The method of claim 17, wherein the evaluating the decolorization effect further includes:

calculating a decolorization rate in a completed time period and predicting a decolorization rate in a future time period according to the chroma image sequence; and evaluating the decolorization effect based on the decolorization rate in the completed time period and the predicted decolorization rate in the future time period.

19. The method of claim 18, wherein the decolorization rate in the future time period is predicted based on a decolorization rate prediction model, the decolorization rate prediction model is a model predicting the decolorization rate in the future time period, the decolorization rate prediction model is a machine learning model.

* * * * *